US008980289B2

(12) United States Patent
Hara et al.

(10) Patent No.: US 8,980,289 B2
(45) Date of Patent: Mar. 17, 2015

(54) INTESTINE IMMUNOMODULATOR

(75) Inventors: Takashi Hara, Niigata (JP); Yuki Higuchi, Niigata (JP); Mikio Fujii, Niigata (JP)

(73) Assignees: Niigata University, Niigata (JP); Kameda Seika Co., Ltd., Niigata (JP)

( * ) Notice: Subject to any disclaimer, the term of this patent is extended or adjusted under 35 U.S.C. 154(b) by 0 days.

(21) Appl. No.: 13/819,262

(22) PCT Filed: May 26, 2011

(86) PCT No.: PCT/JP2011/062138
§ 371 (c)(1),
(2), (4) Date: May 9, 2013

(87) PCT Pub. No.: WO2012/029367
PCT Pub. Date: Mar. 8, 2012

(65) Prior Publication Data
US 2013/0224252 A1  Aug. 29, 2013

(30) Foreign Application Priority Data

Aug. 31, 2010 (JP) ................. 2010-194021

(51) Int. Cl.
*A61K 45/00* (2006.01)
*A61K 39/02* (2006.01)
*A61K 39/00* (2006.01)
*A61K 39/38* (2006.01)
*A61K 47/00* (2006.01)
*A01N 63/00* (2006.01)
*A01N 65/00* (2009.01)
*A23L 1/30* (2006.01)

(52) U.S. Cl.
CPC ............ *A61K 35/747* (2013.01); *A23L 1/3014* (2013.01)
USPC .................. 424/282.1; 424/234.1; 424/184.1; 424/278.1; 424/93.1; 424/93.45

(58) Field of Classification Search
None
See application file for complete search history.

(56) References Cited

FOREIGN PATENT DOCUMENTS

| JP | 2005/139160 A | 6/2005 |
| JP | 2005/194259 A | 7/2005 |
| JP | 2007/308419 A | 11/2007 |
| JP | 2008/179630 A | 8/2008 |
| JP | 2008/201708 A | 9/2008 |
| JP | 2009/292785 A | 12/2009 |
| JP | 2010/057395 A | 3/2010 |
| JP | 2010/130954 A | 6/2010 |
| JP | 2010/150206 A | 7/2010 |
| WO | 2006/087913 A | 8/2006 |
| WO | WO 2007/015132 A2 | 2/2007 |
| WO | 2009/131208 A | 10/2009 |

OTHER PUBLICATIONS

Infectious diseases-Mayo Clinic.com http://www.mayoclinic.com/health/infectious-diseases/DS01145/DSECTION=prevention; pp. 1-9, Accessed on Nov. 8, 2013.*
ESSR issued to EP 11821385.9 mailed Jan. 27, 2014 (full document pp. 1-8).*
ESSR issued to EP Application No. 11821385.9, mailed Jan. 27, 2014.
A.M. Castellazzi et al., "In vitro activation of mononuclear cells by two probiotics: *Lactobacillus paracasei* I 1688, *Lactobacillus salivarius* 11794, and their mixture (PSMIX)," Immunological Investigations, 36:413-421 (2007).
J.G. LeBlanc et al., "A Novel Functional Soy-based Food Fermented by Lactic Acid Bacteria: Effect of Heat Treatment," Journal of Food Science, 69(8):M246-M250 (2004).
Jeremey A. Pena et al., "Probiotic *Lactobacillus* spp. Diminish *Helicobacter hepaticus*-Induced Inflammatory Bowel Disease in Interleukin-10-Deficient Mice," Infection and Immunity, 73(2):912-920 (2005).
Darab Ghadimi et al., Effects of probiotic bacteria and their genomic DNA on TH1/TH2-cytokine production by peripheral blood mononuclear cells (PBMCs) of healthy and allergic subjects, Immunobiology, 2008, vol. 213, pp. 677-692.
Yuichi Kurono et al., "The role of interferon (IFN-gamma) in inducing IgA responses in nasal mucosa against outer membrane protein P6 of nontypeable *Haemophilus influenzae*" Nippon Bika Gakkai Kaishi, 1998, vol. 37, No. 2, pp. 98 to 102, Not Fully translated.
Simona Buccheri et al., IL-4 depletion enhances host resistance and passive IgA protection against tuberculosis infection in BALB/c mice, European Journal of Immunology, 2007, vol. 37, pp. 729-737.
Prosper N. Boyaka et al., IL-12 Is an Effective Adjuvant for Induction of Mucosal Immunity, The Journal of Immunology, 1999, vol. 162, pp. 122-128.

* cited by examiner

*Primary Examiner* — Gary Nickol
*Assistant Examiner* — Lakia Tongue
(74) *Attorney, Agent, or Firm* — Hoffmann & Baron, LLP

(57) ABSTRACT

The purpose of the present invention is to provide a better intestine immunomodulator. The intestine immunomodulator of the present invention comprises bacterial cells or a bacterial component of a *Lactobacillus paracasei* K71 strain having an international deposit No.: FERM BP-11098 as an active ingredient. Preferably, the intestine immunomodulator is used to facilitate production of secretory immunoglobulin A or to activate natural killer cells.

7 Claims, 3 Drawing Sheets

US 8,980,289 B2

INTESTINE IMMUNOMODULATOR

CROSS-REFERENCE TO RELATED APPLICATIONS

This application is the National Stage of International Application No. PCT/JP2011/062138, filed May 26, 2011, which claims the benefit of Japanese Application No. 2010-194021, filed Aug. 31, 2010, the entire contents of both of which are incorporated by reference herein.

TECHNICAL FIELD

The present invention relates to an intestine immunomodulator, and particularly to an intestine immunomodulator containing bacterial cells or a bacterial component of a specific lactic acid bacterium as an active ingredient.

BACKGROUND ART

Secretory immunoglobulin A (SIgA) is an immune substance which exists in mucosal membranes of the oral cavity, the nostril, the respiratory organs, the gastrointestinal tract and the like, and is the core of mucosal immunity. Although the mucosal membranes are constantly exposed to pathogenic bacteria, allergic substances and the like via ambient air and/or foods, the SIgA plays a critical role in protecting the mucosal membrane therefrom. Specifically, the SIgA protects the mucosal membrane by binding to bacteria and/or viruses and agglomerating the same, as well as binding to toxins, enzymes derived from the bacteria, and the like to detoxify them. The amount of the SIgA secreted is under the control of the brain, the endocrine system and the autonomic nervous system, and is lower in the younger and the elderly, compared to the adults.

On the other hand, natural killer (NK) cells are a type of lymphocyte, which finds and kills cells recognized as nonself, such as cancer cells and virally-infected cells. The number of the NK cells is also small at an early age and in the elderly, which is believed to be a cause of the development of infectious diseases in children and the elderly.

In recent years, development of food products and food product components which enhance the amount of the SIgA secreted or the activity of the NK cells has been sought, and specific strains of lactic acid bacteria and bifidobacteria have been reported to exhibit such functions (see, Patent Documents 1 to 8).

Patent Document 1: Japanese Unexamined Patent Application, Publication No. 2005-194259
Patent Document 2: Japanese Unexamined Patent Application, Publication No. 2007-308419
Patent Document 3: Japanese Unexamined Patent Application, Publication No. 2008-179630
Patent Document 4: Japanese Unexamined Patent Application, Publication No. 2008-201708
Patent Document 5: Japanese Unexamined Patent Application, Publication No. 2010-057395
Patent Document 6: Japanese Unexamined Patent Application, Publication No. 2010-130954
Patent Document 7: Japanese Unexamined Patent Application, Publication No. 2010-150206
Patent Document 8: Pamphlet of PCT International Publication No. WO2006-087913

DISCLOSURE OF THE INVENTION

Problems to be Solved by the Invention

However, any of the food products and food product components hitherto developed merely enhances either the secretion of the SIgA or the activity of the NK cells, and cannot enhance both simultaneously. Thus, there exist a concern that the protection of the mucosal membrane is insufficient, or that when the protected mucosal membrane is slightly infected, spread of the symptom caused by the infection cannot be sufficiently suppressed, or the like.

In order for the effect described above to be exerted, it is critical to keep on daily ingesting a food product or food product component exerting such functions. However, in the case of a supplement in the form of a capsule or a tablet, unintentionally forgetting to consume the supplement is a concern, unless a habit of ingesting the supplement is established. In addition, although yogurts and lactic acid bacteria beverages in the form of a general food product can be manufactured using the above-mentioned lactic acid bacteria and bifidobacteria, they are hardly considered to be in the form of an excellent food product for daily ingestion, in that they may be unacceptable depending on the individual consumer's liking, and soon tire the consumer's taste.

On the other hand, rice is a staple food for many people, and it is advantageous if a rice or cooked rice containing a remarkable amount of the lactic acid bacteria exerting the effects as described above can be provided by using the rice as a raw material by way of a process such as fermentation; this is because daily ingestion of such a rice or cooked rice is expected to be highly feasible.

The present invention was developed in view of the above-mentioned situation, and an object of the present invention is to provide a more superior intestine immunomodulator, and specifically, to provide an intestine immunomodulator capable of providing the effect of both facilitating the production of the secretory immunoglobulin A and activating the NK cells, and also capable of being supplied as a processed product of the rice, i.e., the staple food.

Means for Solving the Problems

The inventors found that a lactic acid bacterium, *Lactobacillus paracasei* K71 strain (FERM BP-11098), which possesses anti-allergic effect, vigorously grew on a surface of a grain of rice that had been dipped in water, and the grown lactic acid bacterium strongly bonded to the surface of the grain of rice, resulting in the lactic acid bacterium remaining bound to the grain of rice even after washing and removing the components undesired from the viewpoint of taste, such as lactic acid produced in the fermentation, and that by cooking the washed grain of rice with the lactic acid bacterium attached, there can be produced a cooked rice containing a remarkable amount of the lactic acid bacterium and having good taste organoleptically comparable to an ordinary rice. Based on these findings, the inventors filed an international patent application as PCT/JP2009/059141, detail of which has been internationally published as WO2009/131208. The inventors found that the lactic acid bacterium *Lactobacillus paracasei* K71 surprisingly exerts the effect of both facilitating production of secretory immunoglobulin A and activating NK cells, to accomplish the present invention. More specifically, the present invention provides the following.

A first aspect of the present invention provides an intestine immunomodulator containing bacterial cells or a bacterial component of a *Lactobacillus paracasei* K71 strain having an international deposit No.: FERM BP-11098 as an active ingredient.

In a second aspect of the intestine immunomodulator according to the first aspect of the present invention, the bacterial cells are dead bacterial cells.

In a third aspect of the intestine immunomodulator according to the first or second aspect of the present invention, the intestine immunomodulator is used for facilitating production of secretory immunoglobulin A.

In a fourth aspect of the intestine immunomodulator according to any one of the first to third aspects of the present invention, the intestine immunomodulator is used for activating natural killer cells.

In a fifth aspect of the intestine immunomodulator according to any one of the first to fourth aspects of the present invention, the intestine immunomodulator is orally administered.

In a sixth aspect of the intestine immunomodulator according to any one of the first to fifth aspects of the present invention, the intestine immunomodulator contains a grain of rice fermented with the bacterial cells of the K71 strain, a crushed matter thereof, or a cooked rice obtained by cooking the grain of rice or the crushed matter thereof.

A seventh aspect of the present invention provides a pharmaceutical product which contains the intestine immunomodulator according to any one of the first to sixth aspects of the present invention, and is used for the prevention of an infectious disease.

Effects of the Invention

According to the present invention, the production of the SIgA is facilitated in the mucosal membrane of the airway and the gastrointestinal tract, and the infection of pathogens into a mucosal epithelial cell is prevented through enhanced bonding of the SIgA to the pathogens. Furthermore, even when the mucosal epithelial cell is infected with a virus or the like, the attack of an activated NK cell to the virus prevents further infection of surrounding cells, to enable the prevention of the onset of infectious disease.

PREFERRED MODE FOR CARRYING OUT THE INVENTION

Figure 1:
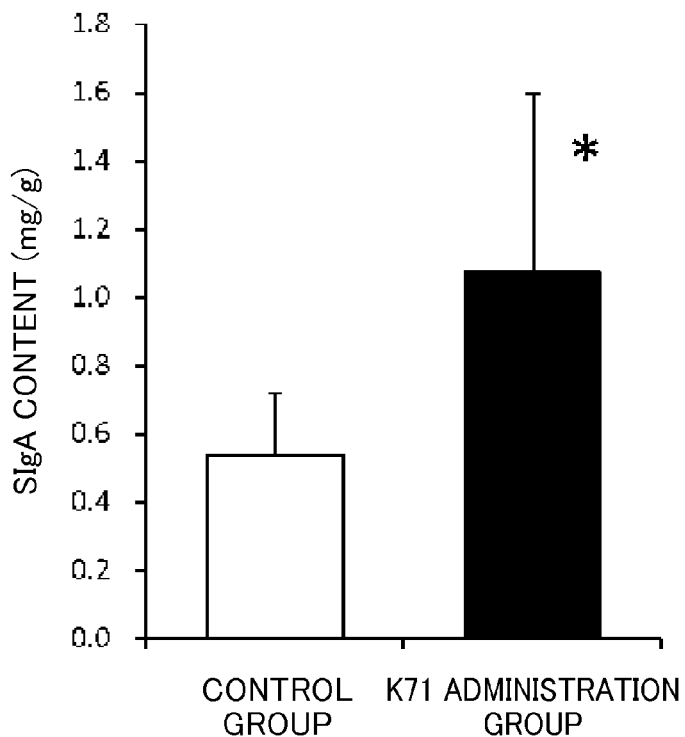
FIG. 1 is a graph comparing the SIgA content in feces of BALB/c female mice when causing the BALB/c female mice to orally ingest a composition produced according to the method according to Example of the present invention for 5 weeks, in which the error bars denote standard deviations, and the asterisk denotes significant difference between groups ($P<0.05$)

Hereinafter, an embodiment according to the present invention will be explained, but the present invention is not limited thereto.

The intestine immunomodulator according to an aspect of the present invention contains bacterial cells or a bacterial component of a *Lactobacillus paracasei* K71 strain having an international deposit No.: FERM BP-11098 as an active ingredient. The bacterial cells and bacterial component exhibit the effect of both facilitating the production of secretory immunoglobulin A, and activating natural killer cells, and are capable of sufficiently preventing infectious diseases.

The term "contain(s) . . . as an active ingredient" used herein is construed not to preclude the inclusion of other components unless the ability to modulate intestine immunity is impaired to the extent that the ability is not statistically significant.

The K71 strain has been internationally deposited in the International Patent Organism Depositary, National Institute of Advanced Industrial Science and Technology (AIST Tsukuba Central 6, 1-1, Higashi 1-chore, Tsukuba-shi, Ibaraki-ken, 305-8566 Japan) on Feb. 20, 2009 under the above-described deposit number. Culturing thereof may be conducted in a standard culture medium (for example, an MRS culture medium, vegetable or fruit juice, or the like) under standard culture conditions. It is preferred to commence the culturing in the culture medium at a pH of 4.0 to 7.0, and preferably 6.0 to 6.5, and to allow the culturing to proceed at a temperature of 35° C. to 42° C., and preferably 37° C. to 40° C. Even Stationary culturing allows for sufficient growth of the bacterial cells; however, it is preferred to gently agitate the culture medium component and the bacterial cells for homogeneous dispersion thereof. As the lactic acid bacterium grows, lactic acid accumulates in the culture medium, which gradually reduces the pH of the culture medium. Although the lactic acid bacterium can be harvested to some extent without adjusting the pH of the culture medium during the culturing, it is preferred to control the pH of the culture medium by adding calcium carbonate to the culture medium, or utilizing an automatic adjustment mechanism. By controlling the pH of the culture medium during the culturing to 4.0 to 7.0, and preferably 6.0 to 6.5, the lactic acid bacterium can be obtained in high density. Other physiological and biochemical characteristics and the like for the K71 strain have been described in WO2009/131208, and therefore, detailed description thereabout is omitted here.

The K71 strain grown in a liquid culture may be utilized as the intestine immunomodulator directly or after drying, and as a starter in fermenting milled rice or the like. In other words, the intestine immunomodulator according to an aspect of the present invention may be produced by the fermentation using the K71 strain. In addition, the K71 strain is predisposed to grow vigorously on a grain of milled rice that has been dipped in water as a single culture medium, and to adhere to a surface of the grain of the milled rice; therefore, production through cooking as well as heating, pressurization and the like may be performed, after removing undesired components such as lactic acid formed during the fermentation from the fermentation product obtained from the rice by the K71 strain, by washing the rice with water.

The bacterial cells may be viable bacterial cells and/or dead bacterial cells, and dead bacterial cells are preferred in view of ensuring a desired extent of the above-described effects. On the other hand, the viable bacterial cells are also preferred in view of the advantages provided by the proliferation or metabolism of the lactic acid bacterium as well as reduction of manufacturing cost of the intestine immunomodulator. It is to be noted that the viable bacterial cells refers to living bacterial cells, whereas the dead bacterial cells refers to bacterial cells which have been subjected to a disinfection treatment through heating, pressurization, treatment with an agent, or the like. Further, the bacterial component refers to a disrupted matter obtained by disrupting the bacterial cells through an enzymatic treatment, homogenization, sonication or the like, or a component which is obtained by fractionating a cell wall fraction from the disrupted matter.

Intended use of the intestine immunomodulator according to an aspect of the present invention is not specifically limited, and it can be used in a broad range of intended uses including modulation of the intestine immunity such as prevention of infectious diseases and health enhancement. However, in light of the identified excellent effects, the intestine immunomodulator according to an aspect of the present invention may be used for facilitating the production of the secretory immunoglobulin A (for example, preventing infection of the mucosal epithelial cell with pathogens) and/or activating the natural killer cells (for example, preventing viral infection from expanding from a certain region of the mucosal epithelial cell to its surroundings).

The intestine immunomodulator according to an aspect of the present invention contains, as an active ingredient, a type of lactic acid bacteria, which have been traditionally incorporated into foods and beverages; therefore, the intestine immunomodulator according to an aspect of the present invention is best suited to oral administration, and may be administered in various dosage forms (a solution, a tablet, granules, and the like). Nonetheless, direct introduction into the intestine via an injection and the like is not precluded.

The intestine immunomodulator according to the present invention as described above is provided with an excellent ability to modulate intestinal immunity as well as safety, and hence is useful as an ingredient of a pharmaceutical product. Accordingly, the present invention encompasses a pharmaceutical product which contains the intestine immunomodulator and is used in the prevention of infectious diseases (for example, so-called common cold). The pharmaceutical product according to an aspect of the present invention is provided with the effect of both facilitating the production of the secretory immunoglobulin A, and activating the NK cells, and hence exerts an excellent infection-preventing effect. It is to be noted that the intestine immunomodulator according to an aspect of the present invention may be combined with a flavoring, a colorant, a preservative, and other components acceptable for food products, to constitute a food product.

EXAMPLES

Example 1

*Lactobacillus paracasei* K71 was seeded in an MRS culture medium, and cultured at 37° C. for 20 hours. The lactic acid bacterial cells were collected by centrifugation, and washed twice with distilled water. To the bacterial cells was added dextrin in an amount equivalent (by weight) to the dried weight of the bacterial cells, and the mixture was pasteurized by heating at 80° C. for 30 minutes. This was freeze-dried to yield a dead bacterial cells powder of *Lactobacillus paracasei* K71 (hereinafter, abbreviated as "K71 powder").

BALB/c female mice (5 weeks of age; purchased from Charles River Laboratories) were acclimatized at 22° C. in a conventional environment for 1 week, and then were divided into two groups (5 mice per group). Twenty mg of the K71 powder was suspended in 1 mL of sterile water, and 50 µL of the suspension was orally administered to one of the groups once a day (1 mg-K71 powder/mouse/day) (K71 administration group). The other group received 50 µL of sterile water in the same way once a day (control group). On the 5th week (on the 34th night to 35th morning) after the start of the rearing, feces of the mice were collected, appropriately suspended in a PBS buffer, and then the amount of IgA (SIgA) contained in the supernatant of the suspension was determined using an ELISA method. The results are shown in FIG. 1.

As can be seen in FIG. 1, the amount of SIgA in the feces of the K71 administration group was significantly higher ($P<0.05$), compared to that of the control group.

Example 2

Figure 2:
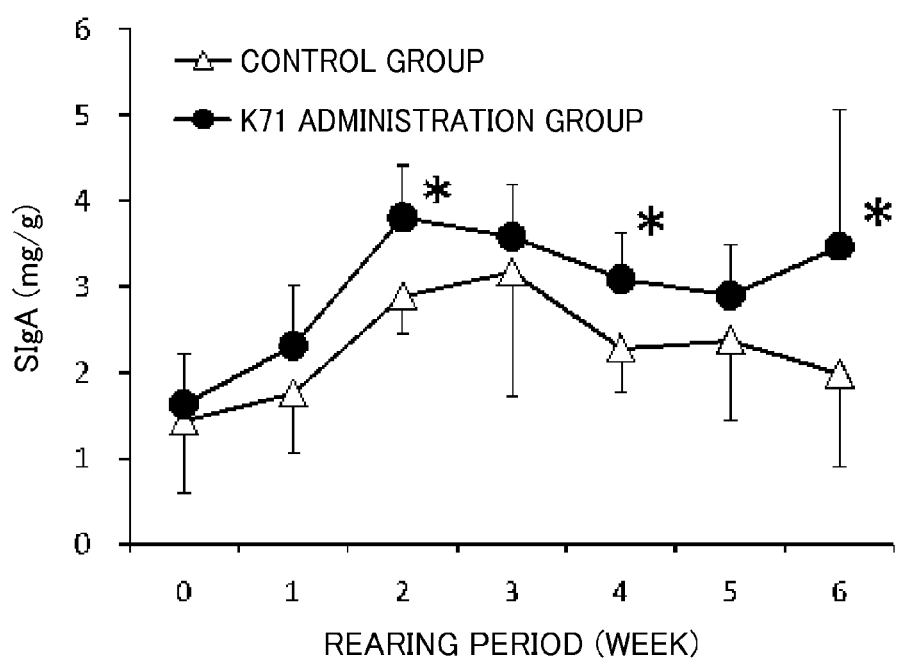
FIG. 2 is a graph showing a week-to-week change in SIgA content in feces of BALB/c female mice when causing the BALB/c female mice to ingest the composition according to the present invention for 6 weeks, in which the error bars denote standard deviations, and the asterisks denote significant difference between groups ($P<0.05$)

Similarly to Example 1, the K71 powder was repeatedly administered orally to BALB/c female mice (6 mice per group) such that each mouse received the K71 powder in an amount of 1 mg/mouse/day, and the amount of the SIgA in their feces was measured once a week. The results showed, as can be seen in FIG. 2, that the K71 administration group consistently exhibited higher SIgA values throughout the testing period, compared to the control group, and the difference therebetween was significant ($P<0.05$) on the 2nd, 4th, and 6th week.

Example 3

Similarly to Example 1, the K71 powder or sterile water was administered daily to BALB/c female mice (6 mice per group). After the completion of rearing for 5 weeks, splenic cells were harvested. The splenic cells ($1.25 \times 10^6$ cells/ml) and YAC-1 cells ($1 \times 10^5$ cells/ml) were mixed in the ratio of 12.5:1 (splenic cells:YAC-1 cells), and the mixture was incubated in RPMI-1640 culture medium containing 1% bovine fetal serum (in a 96-well plate) at 37° C. for 4 hours under a 5% $CO_2$ condition. The cytotoxic activity possessed by the harvested splenic cells was determined by examining the activity of the lactate dehydrogenase (LDH) released upon the disruption of the YAC-1 cells. Specifically, 50 µL of the supernatant of the co-culture of the splenic cells and the YAC-1 cells was transferred to a fresh 96-well plate, and the enzyme activity of the LDH was measured using Cytotoxicity Detection Kit (LDH) manufactured by Roche.

Figure 3:
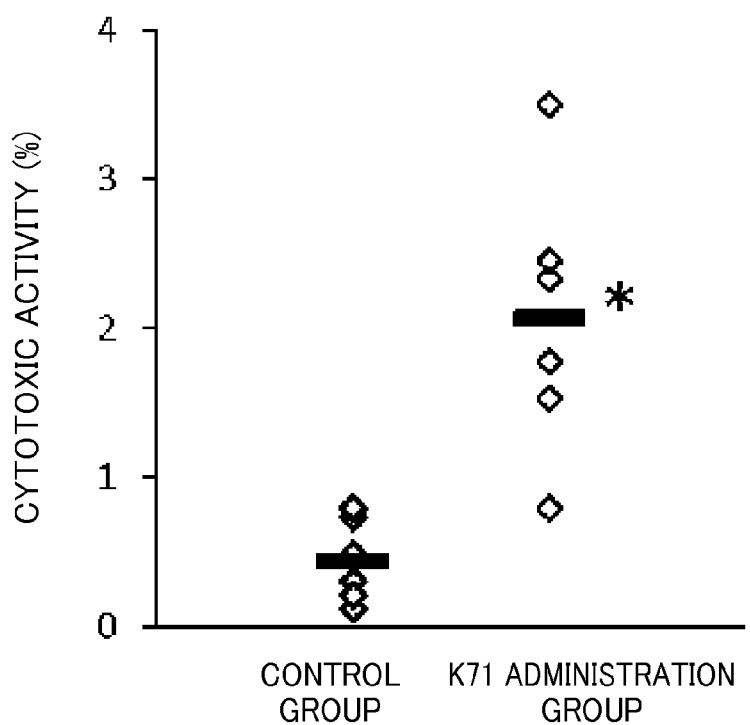
FIG. 3 is a graph showing cytotoxic activity of NK cells contained in the splenic cells of BALB/c female mice after the BALB/c female mice were caused to ingest the composition according to the present invention for 5 weeks, in which the horizontal lines denote average values, the diamonds denote the respective measurement values, and the asterisk denotes significant difference between groups ($P<0.01$)

The results showed that the cytotoxic activity of the splenic cells of the K71 administration group exhibited significantly higher values ($P<0.01$), compared to the control group, as can be seen in FIG. 3. This demonstrated that ingestion of the bacterial cells or bacterial component of the K71 strain promotes the activation of the natural killer cells.

Example 4

SD male rats of 6 weeks age were purchased from SRL, Inc. (Japan), and preliminarily raised for one week under an SPF environment, with ad libitum feeding of a solid feed (FR-2, from Funabashi Farm Co., Ltd.) and tap water. The animals were divided into two groups with 3 mice per group, and raised under the SPF environment at 22° C. for 8 days; the control group received the FR-2 feed, and the K71 administration group received ad libitum feeding of a mixed feed of the FR-2 and the K71 powder (5%). Body weight of the animals was measured before and after the rearing, and additionally their feces were collected immediately before the start of the rearing (from the night before the end of the preliminary rearing to the morning of the last day) and immediately before the end of the rearing (on the 7th night to the 8th morning of the rearing).

The collected feces were appropriately suspended in saline, and subjected to a stomacher treatment, and then the supernatant of the suspension was analyzed for viable cell count (by CFDA fluorescent staining), the number of coliform groups (by a colony counting method using XM-G agar culture medium from Nissui Pharmaceutical Co., Ltd.), and SIgA concentration (by ELISA method). The results are shown in Table 1 and FIG. 4.

TABLE 1

| Item | Control group | | K71 administration group | |
|---|---|---|---|---|
| | Before rearing | After rearing | Before rearing | After rearing |
| Body weight (g) | 251.7 ± 12.9 | 298.3 ± 11.7 | 252.7 ± 2.9 | 301.3 ± 8.5 |
| Body weight difference (g) | 46.7 ± 1.7 | | 48.7 ± 5.5 | |
| weight of feces (g) | 4.2 ± 0.4 | 4.1 ± 0.2 | 4.9 ± 0.3 | 5.0 ± 0.1 |
| Viable cell count (log [CFU]) | 9.53 ± 0.03 | 9.19 ± 0.05 | 9.45 ± 0.04 | 9.33 ± 0.01 |
| Coliform groups (log [CFU]) | 5.24 ± 0.23 | 5.42 ± 0.42 | 4.94 ± 0.34 | 4.65 ± 0.52 |

As can be seen in Table 1, no difference in body weight and body weight gain was observed between the control group and the K71 administration group. Although the weight of the recovered feces was somewhat higher in the K71 administration group, there was no considerable change in weight difference between before and after the rearing. In both groups, the viable cell count in the feces showed only a minor change before and after the rearing.

Figure 4:
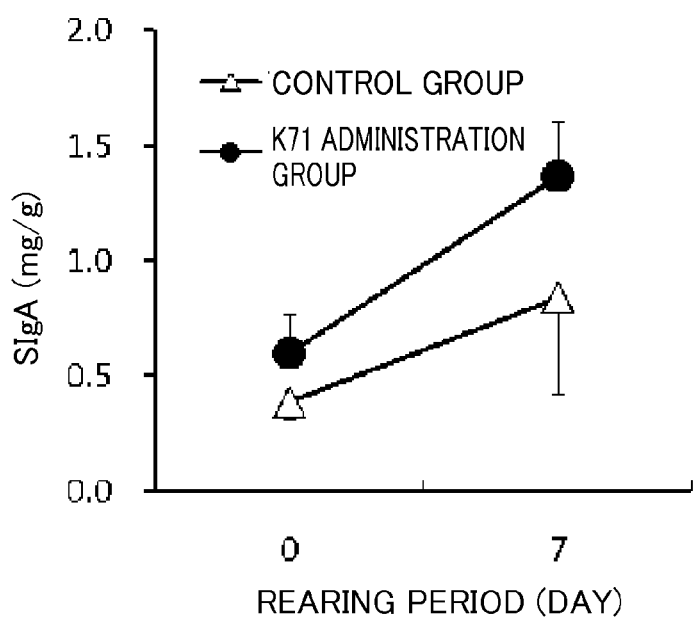
FIG. 4 is a graph showing the increase in SIgA content in feces of SD male rats when the SD male rats was caused to ingest a composition produced according to the method according to Example of the present invention as a dose mixed in feed for 7 days, in which the error bars denote standard deviations.

On the other hand, comparison of the coliform groups in the feces before and after the rearing revealed that the number of the coliform groups decreased in all individuals of the K71 administration group. Furthermore, as with the results in Examples 1 and 2, the amount of the SIgA in the K71 administration group exhibited a higher value, compared to the control group, as can be seen in FIG. 4. This suggested that ingestion of the bacterial cells or bacterial component of the K71 strain promotes the secretion of the IgA in the mucosal membrane of the gastrointestinal tract, thereby resulting in the decrease in the coliform groups in the feces.

Example 5

Figure 5:
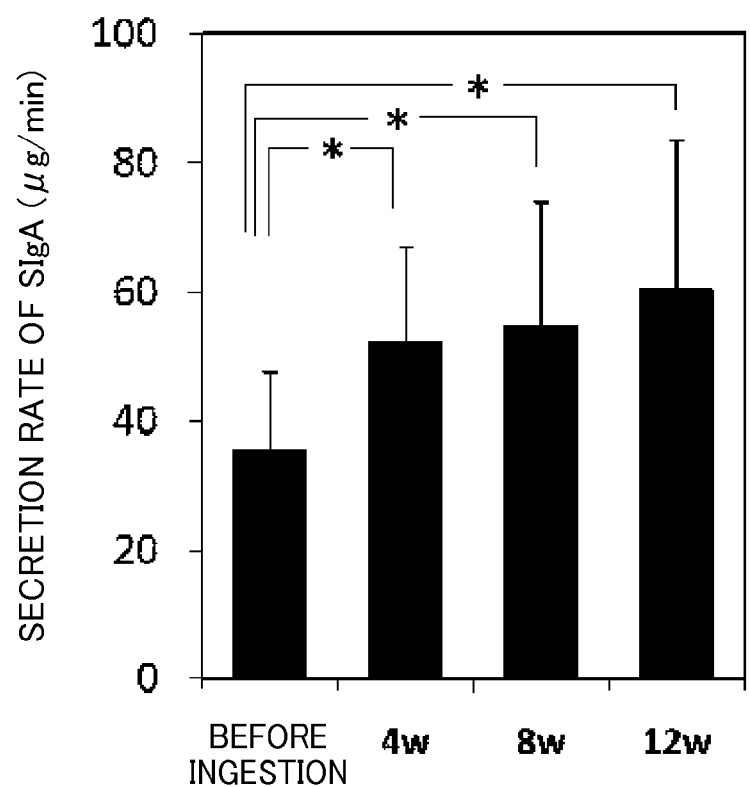
FIG. 5 is a graph showing the increase in rate of the secretion of SIgA in saliva of healthy adult men and women with a relatively low amount of the SIgA secreted when the healthy adult men and women was caused to ingest the composition according to the present invention for 12 weeks, in which the error bars denote standard deviations, and the asterisks denote the significant difference ($P<0.05$) with respect to the value before the start of the testing.

Human studies were conducted in accordance with Declaration of Helsinki and Ethical Guidelines For Epidemiological Research. For twenty-four healthy adult men and women aged between 30 and 57, the rate of secretion of the SIgA in the saliva was measured by a routine method as a pre-ingestion test. The rate of secretion of the SIgA was 47.87±20.07 µg/min. Of the 24 individuals, 11 individuals (five men and six women) with comparatively low rate of secretion of the SIgA were selected as subjects. A test food product (a packaged powdered food product containing 200 mg of the K71 powder per package) was distributed to the subjects, and the subjects were invited to ingest one package a day by mixing it with water, tepid water, or the like. A medical interview and measurement of rate of secretion of the SIgA in the saliva were conducted at the time of visit once every 4 weeks. Two subjects (one man and woman each) abandoned and dropped out of the test in the middle of the test, and thus, analysis was conducted for the remaining 9 subjects. The analysis revealed that the rate of secretion of the SIgA in the 4th, 8th and 12th week after the start of the ingestion was significantly increased compared to the value before the ingestion, as can be seen in FIG. 5. No adverse event due to the ingestion of the tested food was observed throughout the ingestion period.

The invention claimed is:

1. A method for modulating intestine immunity, comprising administering to a subject in need thereof dead bacterial cells of a *Lactobacillus paracasei* K71 strain having an international deposit No.: FERM BP-11098 internationally deposited in the International Patent Organism Depository, National Institute of Advanced Industrial Science and Technology, whereby secretory immunoglobulin A values increase in the subject.

2. The method according to claim 1, wherein the administering activates natural killer cells.

3. The method according to claim 1, wherein the administering is orally conducted.

4. The method according to claim 1, wherein the bacterial cells are administered in forms of a grain of rice fermented with the bacterial cells of the K71 strain, a crushed matter thereof, or a cooked rice obtained by cooking the grain of rice or the crushed matter thereof.

5. The method according to claim 2, wherein the administering is orally conducted.

6. The method according to claim 2, wherein the bacterial cells are administered in forms of a grain of rice fermented with the bacterial cells of the K71 strain, a crushed matter thereof, or a cooked rice obtained by cooking the grain of rice or the crushed matter thereof.

7. The method according to claim 3, wherein the bacterial cells are administered in forms of a grain of rice fermented with the bacterial cells of the K71 strain, a crushed matter thereof, or a cooked rice obtained by cooking the grain of rice or the crushed matter thereof.

* * * * *